United States Patent [19]

Schroeder et al.

[11] Patent Number: 4,739,051
[45] Date of Patent: Apr. 19, 1988

[54] PREPARATION OF MORPHOLINE

[75] Inventors: Wolfgang Schroeder, Bad Durkheim; Wolfgang Lengsfeld, Limburgerhof; Gerd Heilen, Speyer; Otto Hertel, Ludwigshafen; Guenter Boettger, Bad Durkheim, all of Fed. Rep. of Germany

[73] Assignee: BASF Aktiengesellschaft, Ludwigshafen, Fed. Rep. of Germany

[21] Appl. No.: 16,484

[22] Filed: Feb. 17, 1987

Related U.S. Application Data

[63] Continuation of Ser. No. 651,642, Sep. 17, 1984, abandoned, which is a continuation of Ser. No. 392,706, Jun. 28, 1982, abandoned.

[30] Foreign Application Priority Data

Jun. 30, 1981 [DE] Fed. Rep. of Germany ....... 3125662

[51] Int. Cl.$^4$ ............................................ C07D 295/02
[52] U.S. Cl. .................................. 544/106; 540/612; 546/184; 548/579
[58] Field of Search ........................ 544/106; 546/184

[56] References Cited

U.S. PATENT DOCUMENTS 2,529,923 11/1950 Dickey et al. ...................... 544/106
3,151,112 9/1964 Moss ................................. 544/106

FOREIGN PATENT DOCUMENTS 0036331 9/1981 European Pat. Off. .

Primary Examiner—Robert W. Ramsuer
Attorney, Agent, or Firm—Keil & Weinkauf

[57] ABSTRACT

Morpholine and other cyclic imines are obtained by reacting diethylene glycol and other appropriate diols with ammonia under hydrogenating conditions in the gas phase in the presence of a catalyst which contains copper, a smaller amount of nickel and alumina.

4 Claims, No Drawings

PREPARATION OF MORPHOLINE

This application is a continuation of application Ser. No. 651,642 filed Sept. 17, 1984, now abandoned which is a continuation of Ser. No. 392,706 filed June 28, 1982, now abandoned.

The present invention relates to a novel process for the preparation of cyclic imines and to a catalyst for this process.

Cyclic imines, e.g. pyrrolidine, piperidine, morpholine and azepine, are valuable intermediates for diverse purposes, for example for the preparation of crop protection agents and drugs.

Morpholine, which is also used as a vulcanizing assistant, is, from the point of view of quantity, the most important of the cyclic imines. Accordingly, in the description which follows, the preparation of morpholine is emphasized.

In the conventional industrial processes for the preparation of morpholine, the starting material is either diethanolamine, from which morpholine is obtained by elimination of water, or diethylene glycol (diglycol), from which aminodiglycol is produced by adduct formation with ammonia, accompanied by elimination of water, the aminodiglycol immediately reacting further, with additional elimination of water and cyclization, to give morpholine. Similar processes are used to convert butanediol to pyrrolidine and hexanediol to azepine (hexamethyleneimine).

These reactions are conventionally carried out either over a finely divided catalyst in excess diol, in which case the presence of hydrogen can be advantageous, or over a fixed catalyst bed. The process is usually carried out under high pressure, in general under form 70 to 350 bar, and when a fixed bed is employed for the reaction of diethylene glycol the latter is passed in the liquid phase over the catalyst.

A fixed bed is also used if the reactants are to be passed in gaseous form over the catalyst. The catalysts employed for this purpose are either pure nickel catalysts (Japanese Patent Application No. 71/31,863 and Russian Patent No. 175,512), or contain nickel together with other metals (Japanese Patent Application Nos. 74/032,699 and 74/032,189, and German Patent No. 2,758,769).

The disadvantage of nickel catalysts is that the yield of imine is poor, namely from about 50 to 80%.

We have found that cyclic imines can be prepared in high yield by reacting a diol with ammonia under hydrogenating conditions in the presence of a mixed catalyst based on copper and nickel supported on alumina, if the amination is effected in the gas phase over a catalyst which in addition to copper contains from 2 to 50% by weight, based on copper, of nickel and/or cobalt, the carrier being alumina, and which has been obtained by precipitating the salts of copper, nickel and/or cobalt and aluminum, capable of precipitation with an alkali metal carbonate, by means of an aqueous solution of such a carbonate and, using conventional methods, molding the precipitate, drying it and activating it with hydrogen.

As active components, the catalyst contains predominantly copper, together with nickel and/or cobalt. The total content of these metals is from 10 to 70% by weight, the remainder being essentially accounted for by alumina, and the content of nickel and/or cobalt is from 2 to 50% by weight, based on the amount of copper.

With an increasing proportion of nickel, the reaction becomes increasingly non-specific; thus, for example, substantial amounts of methylglycol are formed from diethylene glycol. If, on the other hand, a nickel-free catalyst is used, the activity of the catalyst is inadequate. Cobalt can be used in place of nickel, but is less advantageous, not least for economic reasons.

The catalyst can be prepared in accordance with the general method given in German Patent No. 2,445,303, which is herewith incorporated by reference.

For use as a fixed bed, the catalyst can be in the form of cylindrical tablets, extrudates of circular or other cross-sections, or various other shapes. For use as a fluidized bed, which is also possible, the catalyst is employed as a powder.

Advantageously, a nitrogen/hydrogen mixture, containing 10% by volume of hydrogen, is used to reduce the copper and nickel oxides to the metals. The copper oxide is reduced at from 140° to 180° C. To reduce the nickel oxide, the temperature is raised to as much as 300° C.

The catalyst is also useful for other syntheses classifiable as aminating hydrogenations.

The cyclic imines obtainable by the process according to the invention preferably have from 5 to 7 ring members, examples being pyrrolidine, piperidine, azepine and morpholine. The imines can also be substituted by several lower alkyl groups.

Examples of diols suitable for the reaction are propane-1,2-diol, butane-1,4-diol, pentane-1,5-diol, hexane-1,6-diol and diethylene glycol.

The reaction pressure required in the novel process is less than 100 bar, and in most cases less than 30 bar. The vaporization and reaction temperature is from 170° to 250° C., especially from 200° to 250° C. The best yield achievable depends of course on the particular catalyst used, and is in general obtained over a relatively narrow temperature range.

The total effective gas flow rate employed is, for example, from 100 to 1,000 parts by volume per part by volume of the catalyst per hour. The gas stream contains, for example, from 20 to 70% by volume of ammonia. In general it is advisable to use as little ammonia as possible.

A suitable reaction apparatus is a shaft furnace or, preferably, a tube reactor. A downward direction of flow is preferred.

The process is preferably carried out as follows: a compressor is used to maintain a stream of gas, consisting essentially of hydrogen, which successively flows through a vaporizer, the reactor, a condenser and a separator, and is then drawn in again by the compressor. The diol and ammonia are fed to the vaporizer. The conditions in the vaporizer, in respect of pressure, temperature and amounts, are balanced so that the diol is vaporized completely and a molar ratio of ammonia: diol of, for example, from 10 to 100 is obtained.

The reaction temperature depends, within certain limits, on the ratio of copper to nickel in the catalyst. In every case, the following general relationships apply: below the optimum temperature, the crude reaction product contains unconverted diol as well as reactive intermediates: with decreasing temperature, the proportion of these increases. Above the optimum temperature, the crude reaction product contains cleavage products, principally methylglycol if diethylene glycol is used, and the proportion of these products increases with increasing temperature. The most advantageous temperature range is relatively narrow, namely a span of about 10°–20°, and is usually to be found between 200° and 250° C. These limits can be adhered to most simply when a tube reactor is used, and such a reactor is accordingly preferred for carrying out the process. The most advantageous temperature, flow rate, etc., are established by preliminary experiments.

When the reaction product is condensed, a part of the unconverted ammonia goes into solution. The amount of ammonia fed to the vaporizer must accordingly replace both this dissolved part and the chemically converted part. The dissolved part is separated from the reaction product by distillation and returned to the recycle gas. In an advantageous case, the reaction product in general contains less than 2% of unconverted diol, together with not more than 10% of intermediates which are higher-boiling than the imine; when diethylene glycol is used, these intermediates are especially morpholinyldiglycol, morpholinyldiglycolamine and dimorpholinyldiglycol. In a particular embodiment of the novel process, these intermediates, which can easily be separated off, are recycled, together with the fresh diol, to the vaporizer and reactor, since they are ultimately converted to the imine. In this way a selectivity, based on diol, of about 95% is achieved.

EXAMPLE 1

Preparation of the catalyst

About 2-molar aqueous solutions are prepared from commercial copper nitrate, nickel nitrate and aluminum nitrate, and are combined with one another, in such amounts that the metals copper, nickel and aluminum are present in the mixture in an atomic ratio of 4:1:6.

A 2-molar aqueous solution is also prepared from commercial sodium carbonate.

The two solutions are brought to 80° C. and combined over 2 hours in a stirred kettle at such a rate that the pH is always 7–8. A precipitate forms and is filtered off and washed with salt-free water until it is virtually free from nitrate and sodium ions. The crude catalyst mass obtained is dried and molded into cylindrical tablets 4.7 mm high and of 4.7 mm diameter, which are heated at 600° C. 1 liter of this catalyst intermediate is introduced into a tube reactor of 45 mm diameter, surrounded by a jacket through which a heat transfer medium flows.

Apparatus

Above the reactor there is a vaporizer, and also a temperature-balancing zone in which the gas mixture can be brought to the reaction temperature.

Below the reactor is a condenser in which the reaction mixture can be cooled to about 20° C., and which, in turn, is followed by a separator. The uncondensed gas can be recycled, by means of a compressor, to the vaporizer, to which the other reactants are also fed.

Activating the catalyst

Before the reaction is started, the catalyst intermediate is converted to the true catalyst by reduction with hydrogen. A mixture of 10% by volume of hydrogen and 90% by volume of nitrogen is passed over the catalyst at 140° C. for 8 hours, the temperature is then raised to 180° C. over 4 hours, and the reduction is continued for a further 4 hours at the latter temperature. Finally, the nitrogen is replaced by hydrogen and the temperature is raised to 300° C. The reduction is complete after a further 8 hours.

Reaction

The pressure in the apparatus is brought to 8 bar. Using the compressor, a mixture of 50% by volume of hydrogen and 50% by volume of ammonia, in an amount of 4 m$^3$ (S.T.P.), is continuously circulated through the apparatus by pumping. The temperature in the reactor is set to 210° C. 0.2 liter per hour of diglycol is then fed to the vaporizer.

The condensate collected in the separator is analyzed by gas chromatography and worked up by fractional distillation.

After deducting ammonia and water, the product contains 93% by weight of morpholine, 3% by weight of methylglycol and 4% by weight of imtermediates.

EXAMPLE 2

The catalyst from Example 1 is used, and the reaction apparatus is a cylindrical heated tube of 800 ml capacity. The catalyst bed is brought to 200° C., and 250 liters (S.T.P.) of hydrogen per hour are passed through the bed at atmospheric pressure. Per hour, 90 liters (S.T.P.) of gaseous ammonia and 80 ml of 1,2-dipropylene glycol (isomer mixture) are fed to the vaporizer, through which the hydrogen flows.

The reaction product is condensed, collected in the separator, analyzed by gas chromatography and subjected to fractional distillation.

Conversion is complete and the reaction product, (after deduction of water and ammonia) contains 97% of dimethylmorpholine (isomer mixture) and 3% of unknown substances.

EXAMPLE 3

The procedure followed is as in Example 1, except that, in place of diethylene glycol, technical-grade 96% pure pentane-1,5-diol is fed to the vaporizer.

The condensate collected in the separator is analyzed by gas chromatography and subjected to fractional distillation.

After deduction of ammonia and water, the product contains 92% by weight of piperidine; this is equivalent to a yield of 95%, based on the pentanediol in the starting material.

We claim:

1. A process for the preparation of morpholine, which comprises:
   reacting diethyleneglycol with ammonia in the gas phase at a temperature of about 200° to 200° C., under hydrogenating conditions in the presence of a mixed catalyst of copper and nickel on an alumina carrier, said catalyst containing from 2 to 50% by weight, based on the copper, of nickel, said catalyst having been formed by precipitating salts of copper and nickel and aluminum that are capable of precipitation with an alkali metal carbonate by contacting said salts with an aqueous solution of such carbonate, molding and drying the formed precipitate and activating the precipitate with hydrogen.

2. The process of claim 1, wherein the catalyst is prepared from copper nitrate, nickel nitrate and aluminum nitrate.

3. The process of claim 1, wherein the catalyst has a content of copper and nickel from 10 to 70% by weight, the remainder consisting essentially of alumina.

4. The process of claim 3, wherein the reaction pressure is less than 100 bar.